United States Patent [19]

Mendoza-Frohn et al.

[11] Patent Number: 5,489,696

[45] Date of Patent: Feb. 6, 1996

[54] PROCESS FOR PURIFYING ETHYLENE GLYCOL CARBONATE (EGC) BY ADSORPTION ON ACTIVATED CARBON

[75] Inventors: Christine Mendoza-Frohn, Erkrath; Paul Wagner, Düsseldorf; Hans-Josef Buysch, Krefeld, all of Germany

[73] Assignee: Bayer Aktiengesellschaft, Leverkusen, Germany

[21] Appl. No.: 421,726

[22] Filed: Apr. 13, 1995

[30] Foreign Application Priority Data

Apr. 22, 1994 [DE] Germany ............... 44 14 121.1

[51] Int. Cl.⁶ ................................. C07D 317/08
[52] U.S. Cl. ................................................ 549/230
[58] Field of Search ................................. 549/230

[56] References Cited

U.S. PATENT DOCUMENTS

| | | | |
|---|---|---|---|
| 2,773,881 | 12/1956 | Dunn | 260/340.2 |
| 2,994,705 | 8/1961 | Crosby et al. | 260/340.2 |
| 3,025,305 | 3/1962 | Verdol | 260/340.2 |
| 4,314,945 | 2/1982 | McMullen et al. | 260/340.2 |
| 5,350,862 | 9/1994 | Wagner et al. | 549/230 |
| 5,391,767 | 2/1995 | Mais et al. | 549/229 |

FOREIGN PATENT DOCUMENTS

| | | |
|---|---|---|
| 1226117 | 10/1966 | Germany . |
| 2855232 | 6/1979 | Germany . |
| 4138438 | 5/1993 | Germany . |
| 4141189 | 6/1993 | Germany . |
| 4210943 | 10/1993 | Germany . |

OTHER PUBLICATIONS

Chemical Abstracts, vol. 66, abstract No. 28389v, abstract of DE 1,226,117 (1967).

G. Hechler, Chemie, Ing. Techn, vol. 43, No. 16, pp. 907–905 (1971).

H. Springmann, Fette, Seifen, Anstrichmittel, vol. 73, No. 6 pp. 396–399 (1971).

Ullmann's Encyclopedia of Industrial Chemistry, 4th ed, vol. 2, pp. 600–619 Verlog Chemie (1973).

Ullman's Encyclopedia of Industrial Chemistry, 5th Ed., vol. A5 pp. 124–140 (1986).

*Primary Examiner*—C. Warren Ivy
*Assistant Examiner*—Amelia Owens
*Attorney, Agent, or Firm*—Sprung Horn Kramer & Woods

[57] ABSTRACT

Ethylene glycol carbonate (EGC) can be obtained in purified form from contaminated material which contains impurities from the production or work-up process, by subjecting it to treatment with activated carbon. The treatment is carried out at 40°–250° C. and at 1–200 bar. The activated carbon has a BET surface area of 200–3,000 $m^2/g$.

17 Claims, No Drawings

PROCESS FOR PURIFYING ETHYLENE GLYCOL CARBONATE (EGC) BY ADSORPTION ON ACTIVATED CARBON

BACKGROUND OF THE INVENTION

1. Field of the Invention

The present invention relates to a process for purifying ethylene glycol carbonate (EGO) containing impurities from the production or work-up process, by treatment with activated carbon.

The process makes possible, for example, the purification of an EGC stream which is bled from the reaction circuit for producing EGC for the purpose of avoiding an accumulation of byproducts.

The process allows the virtually complete recyclability of this purified EGC side-stream in the EGC production and work-up circuit and thereby contributes to a material-saving mode of operation in the production of EGC.

2. Description of the Related Art

It is known that EGO can be prepared in various ways, for example from ethylene glycol and phosgene (DE-AS (German Published Specification) 1 226 117), from ethylene oxide or ethylene chlorohydrin and carbon dioxide (Chem. Ing. Techn. 43 (1971), 903 ff; Fette, Seifen, Anstrichmittel 73 (1971), 396 ff; DE-OS (German Published Specification) 2 855 232, corresponding to U.S. Pat. No. 4,314,945; Ind. Eng. Chem. 50 (1958), 767–770; DE-OS (German Published Specification) 4,141,189, DE 4,138,438; DE 4,210,943) and also from ethylene, oxygen and carbon dioxide (U.S. Pat. No. 3,025,305). The EGC is here generally obtained in a form contaminated by the various materials from the production process and secondary components.

In the process starting from ethylene oxide and carbon dioxide, the crude product further contains the dissolved catalyst, for example quaternary ammonium compounds, alkali metal halides or alkali metal halides in combination with zinc halides. This has to be removed from the crude product prior to final purification, e.g. by fractional distillation. Thus, for example, in the process described in Chem. Ing. Techn. and Fette, Seifen, Anstrichmittel (loc. cit.), two thin-film distillations are carried out to remove the catalyst prior to the final purification. This separated catalyst can then mostly be recycled to the production reaction for EGC. In this thin-film distillation, the EGC is partially decomposed, even if mild conditions (maximum 50 mbar) are maintained. The decomposition products collect, depending on volatility, in the distillate or in the liquid phase of the distillation. The danger of decomposition of the EGC is due, in particular, to the fact that the catalyst is concentrated in the liquid phase of the distillation as a result of the pure EGC distilling off and that the degree of decomposition of the EGC is strongly dependent on the concentration of the catalyst dissolved therein. Thus, for an inlet concentration of from 0.25 to 0.5% by weight of catalyst, not more than from 90 to 95% of the EGC may be distilled off. In addition, the catalyst itself can be decomposed in this distillation process. If it is desired to recycle the liquid phase of the distillation, which represents a concentrated catalyst solution, into the production reaction, a part of the catalyst has to be discarded and replaced by new catalyst. Thus, for example, replacement of 30% of the catalyst solution is recommended. The replacement of the catalyst solution is carried out by bleeding off a part of the catalyst solution from the EGC production and work-up circuit and simultaneously feeding in the corresponding amount of fresh catalyst (Ind. Eng. Chem., loc. cit; DE 4,141,189).

In addition, the bleeding procedure avoids an accumulation of impurities, e.g. higher-boiling secondary components, which can be formed during the reaction and the work-up.

The bleed stream can, depending on the conditions of EGC production and work-up, comprise up to $\geq 90\%$ of EGC and therefore represents a significant loss in yield if it has to be discarded.

This is particularly true when production and work-up are carried out under gentle conditions, for example by adiabatic preparation of the EGC as in DE 4,141,189 using relatively low pressures and low separation rates in the vacuum distillation. In such gentle production and workup, the bleed stream can even be about 99% EGC.

It was therefore desirable to have a purification process for EGC contaminated by higher-boiling secondary components and possibly laden with catalyst from the EGC production process, which purification process leads to as complete as possible removal of the secondary components but only to low catalyst losses. Furthermore, the purification process should itself represent no stress on EGC and catalyst and be energy conserving.

SUMMARY OF THE INVENTION

It has now surprisingly been found that in the treatment with activated carbon of EGO crude products or of EGC catalyst solutions contaminated with higher-boiling secondary components from the EGC production or work-up process, the secondary components can be virtually completely removed from the EGC while the catalyst is only adsorbed to a small extent on the activated carbon. In this way, the incineration of the bleed stream comprising from 90 to about 99% EGC can be avoided and the purified stream can be recycled to the production process. The small proportion of the catalyst adsorbed on the activated carbon has to be replaced by fresh catalyst when recycling the purified EGC to the reaction circuit. This replacement of a small proportion of adsorbed catalyst can even be desired if any catalyst deactivation occurring during the reaction and work-up is thereby compensated.

A further advantageous effect of the purification of the invention of EGC by adsorption is that the purification step itself represents no additional stress on EGC and catalyst.

The invention accordingly provides a continuous or batchwise process for purifying ethylene glycol carbonate (EGC) containing impurities from the production or work-up process of the EGC, which is characterized in that the contaminated EGC is subjected at 40°–250° C., preferably 40°–200° C., particularly preferably 40°–160° C., and at 1–200 bar, preferably 1–100 bar, particularly preferably 1–30 bar, to a treatment with activated carbon having a BET surface area of 200–3,000 $m^2/g$, preferably 300–2,000 $m^2/g$, particularly preferably 500–1,500 $m^2/g$.

DETAILED DESCRIPTION OF THE INVENTION

The contaminated EGC to be used according to the invention can be either a pre-purified EGC which is to be subjected to a further final purification step, or a crude reaction mixture which originates directly from the production process of the EGC. Owing to the abovedescribed virtually complete removal of the higher-boiling secondary components with, at the same time, only low adsorption of the catalyst, the purification method is particularly suitable for the work-up of the bleed stream which is taken from the reaction and work-up circuit to avoid byproduct accumulation and which nevertheless comprises predominantly EGC.

In a furthermore advantageous manner, the purification process can then serve for the simultaneous removal of a proportion of catalyst for the purpose of replacing deactivated catalyst.

The accumulation rate of secondary components in the circuit from reaction and work-up and thus the bleed stream necessary to avoid secondary component accumulation are known to those skilled in the art. The purification using activated carbon can, as a function of the reaction parameters (such as, for example, residence time) achieve virtually complete removal of the secondary components from the bleed stream in a manner known to those skilled in the art. The adsorption of the catalyst on the activated carbon, which occurs to a very small extent, likewise depends on the selected parameters for adsorption. However, for the purpose of replacing deactivated catalyst, an amount of catalyst, which is easy to determine in the individual case, has to be removed from the circuit.

Accordingly, it can be judged whether the bleed stream is to be conducted completely or only partly through the activated carbon purification and whether in this purification complete removal of the secondary components is to be brought about by appropriate selection of the parameters.

In a furthermore preferred manner, the bleed stream is taken from the residue of the work-up, since here the concentration of secondary components is the highest and a purification of the bleed stream is the most effective. In the work-up by vacuum distillation, the residue corresponds to the liquid phase of distillation. However, other work-up methods for the EGC are also conceivable, and the purification of the bleed stream is then likewise useful and able to be carried out. For example, purified EGC can be obtained by fractional melt crystallization from a contaminated EGC which contains impurities from among starting materials, byproducts and/or catalysts of the production process. In this method, the crystallizate formed represents the purified EGO, the remaining melt in which the impurities are dissolved represents the residue to be recycled.

Combinations of work-up methods are likewise conceivable, for example a melt crystallization and a subsequent vacuum distillation of the crystallizate. In this case, the melt from the crystallization and the liquid phase from distillation can be recycled to the production process and represent the appropriate point within the process for taking the bleed stream.

Preferably, the EGC stream purified by adsorption on activated carbon is recycled to the production circuit. The process of the invention for purifying EGC by adsorption on activated carbon can be carried out either with batchwise or with continuous contacting of the activated carbon with the EGC to be purified; preferably it is carried out with continuous contacting.

For the purification according to the invention of EGC by adsorption on activated carbon, the adsorption processes used can be as described, for example, in Ullmann's Enzyklopädie der technischen Chemie, 4th edition, Vol. 2, pp. 600–619 and in the literature cited therein and known to those skilled in the art. These are, for example, fixed-bed processes in which the activated carbon is fixed and the starting material to be purified flows through it downwards or else from the bottom upwards, either in the flooded state or as a trickle phase. In terms of the construction of the fixed-bed adsorber, a distinction is made between, for example, horizontal or vertical adsorbers and simple adsorption tanks. Other adsorption processes instead operate using moving adsorbents, for example in a moving bed or in a fluidized bed. When using pulverulent activated carbons, distinction is made between stirring-in processes in which the adsorbent is stirred with the starting material to be purified in a stirred vessel and is subsequently filtered off in a filter press, and the filter bed process in which an adsorbent bed is first produced by suspension on the filter, and the starting material to be purified is pressed through the bed.

For purification of EGC according to the invention by adsorption on activated carbon, preference is given to using fixed-bed processes. Advantageously, two adsorption beds are provided, so as to be able, on exhaustion of the one adsorption bed, to switch over to the other and regenerate or replace the used activated carbon. Depending on the process selected, the purification of the EGC by adsorption according to the invention has to be followed by a filtration step.

The parameters, such as temperature, pressure, residence time, to be set in the purification of EGC by adsorption according to the invention are dependent on the selection of adsorption process and influence the result of purification in a manner known to those skilled in the art. For example, a temperature above the melting point of EGC, i.e. above about 40° C., has to be maintained during the purification of EGC. The maximum possible temperature is the boiling point of EGC, i.e. 250° C. Since EGC, in particular in the presence of catalysts, can decompose at a higher temperature, it is advisable also to use higher pressures when a higher temperature is selected.

Thus, in principle, an adsorption temperature of from 40° to 250° C., preferably from 40° to 200° C. and particularly preferably from 40° to 160° C., is to be set. The pressure should be in the range from 1to 200 bar, preferably from 1 to 100 bar, particularly preferably from i to 30 bar.

The purification of EGC by treatment with activated carbon according to the invention is preferably carried out with exclusion of moisture.

For the purposes of the present invention, the activated carbon can be prepared from various, carbon-generating precursors. The processes for conversion into the active form can likewise be very different. Such production processes give activated carbons which have BET surface areas of from 200 to 3,000 $m^2/g$, preferably from 300 to 2,000 $m^2/g$, particularly preferably from 500 to 1,500 $m^2/g$, and bulk densities between 250 and 550 g/l. Examples which may be mentioned of starting materials for preparing activated carbons are: sawdust and other wood wastes, straw, various types of coal, such as bituminous or brown coal, nut shells, mineral oil tars, lignin,polysaccharides, polyacrylonitrile, bones and peat. Furthermore, it is also possible to use coke products from brown and black coals. Preferred examples which may be mentioned are: wood, cellulose, lignin, bituminous or brown coal, peat or black coal coke.

The carbon-generating precursors mentioned can be activated by various methods, for example by chemical activation using phosphoric acid or zinc chloride, by gas activation using steam, oxygen or nitrous gases. Such preactivated precursors are then converted thermally, i.e. by coking, into activated carbons for the process of the invention. These production methods are known to those skilled in the art and, exactly like the detailed description of the various sorts of activated carbon thus obtainable, are comprehensively described in the literature (see Ullmann's Encyclopedia of Industrial Chemistry, 5th, Edition, Vol. A5 (1986), pp. 124–140 and the references cited therein).

With regard to the form used, shaped carbons, crushed carbons and pulverulent carbons can be used in the process of the invention. In the case of shaped carbons, which are usually produced by extrusion from powders and then have a cylindrical shape or, more rarely, are present as pellets, suitable diameters are usually in the range from one to a few mm. In the case of pulverulent carbons, attention has to be paid, in particular, to sufficient filterability.

Those skilled in the art will be familiar with the optimum shape of the activated carbon to be used depending on the choice of adsorption process.

Regeneration is frequently not worthwhile. The adsorbed salts and colour-producing compounds can, if desired, be washed from the activated carbon using water, methanol, methanol/water, glycol or glycol/water mixtures and in this way regeneration can be achieved. In a continuous procedure, the activated carbon used can remain in the adsorber for a long time. Insoluble organic deposits can be removed by passing over superheated steam, optionally with addition of subordinate amounts of air (from about 0.1 to 20% by weight, based on the amount of steam used) at from 150° to 800° C. or by passing over from 0.01 to 5% by weight of oxygen-containing dilution gases such as nitrogen, carbon monoxide or carbon dioxide or by carbon dioxide alone at from 200° to 800° C. The preferred regeneration temperarespectively, samples of the EGC were taken and, after separating off residues of activated carbon, the Hazen colour number and the catalyst content were determined.

The following five activated carbons were tested:
A: Norit R 2030, A-9421* ($\propto$2 mm, rods/675 m$^2$/g)
B: Norit R2, A-5997* ($\propto$1.5 mm, rods/1100 m$^2$/g)
C: Norit RB1, A-9661* ($\propto$1 mm, rods/1000 m$^2$/g)
D: Sorbonorit 2, A-8008* ($\propto$1.5 mm, rods/1250 m$^2$/g)
E: Chemviron CPG LF** (1–2 mm, granulated/1000 m$^2$/g)

In the five experiments, an identical EGC grade having a colour number of 400 and NaBr and $ZnBr_2$ loadings of the catalyst of 0.22 mol % of NaBr and 0.11 mol % of $ZnBr_2$ was used. The quality of this starting EGC was, at 99.02% EGC according to GC analysis, already very high.

Table 1 shows the results of the 5 experiments 1A to 1E. As measure of the adsorption of the catalyst on the activated carbon, the concentration of $ZnBr_2$ in the purified EGC solution is shown here.

Purification of EGC using various activated carbons Carbons A to E; Ratio: 1 part of activated carbon/5 parts of EGC; 50°–60° C.
* Commercial product of Norit
** Commercial product of Calgon

| Residence time (h) | Hazen colour number | | | | | mol % $ZnBr_2$ (AAS) | | | | |
| --- | --- | --- | --- | --- | --- | --- | --- | --- | --- | --- |
| | A | B | C | D | E | A | B | C | D | E |
| Starting material | | | 400 | | | | | 0.11 | | |
| 0.5 | 400 | 250 | 250 | 190 | 80 | 0.108 | 0.106 | 0.100 | 0.103 | 0.092 |
| 1 | 400 | 200 | 200 | 190 | 50 | 0.107 | 0.104 | 0.096 | 0.097 | 0.095 |
| 3 | 375 | 180 | 180 | 170 | 30 | 0.106 | 0.099 | 0.087 | 0.097 | 0.120 |
| 24 | 225 | 100 | 120 | 100 | 20 | 0.093 | 0.089 | 0.074 | 0.091 | 0.080 | ture is from 250° to 700° C., particularly preferably from 250° to 600° C.

EXAMPLES

The following examples demonstrate the continuous and the batchwise contacting of the activated carbon with the EGC to be purified and likewise the effect of the activated carbon adsorption on the catalyst dissolved in the EGC to be purified.

The composition of the EGC catalyst solution and the purified EGC were determined by gas chromatography. As a sensitive measure for the colour purity of crude and pure product, use was made of the Hazen colour number which quantifies the yellow cast, for example attributable to the polycondensed downstream products of acetaldehyde, in the EGC samples.

The catalyst concentrations in crude and pure EGC were determined, when using inorganic salts, by means of atomic absorption spectroscopy, in the case of the ammonium halide as catalyst, by argentometric titration.

EXAMPLE 1 (Table 1)

In experiments carried out batchwise, 5 parts of EGC catalyst solution and 1 part of activated carbon (weight ratio) were in each case contacted with one another at from 50° to 60° C. while stirring. After 30 minutes, 1, 3 and 24 hours The following facts can be derived from Example 1:
For the purification of EGC by adsorption according to the invention, various activated carbons are suitable,
For the purification of EGC, the most suitable of the carbons examined here is the activated carbon Chemviron CPG LF. After only 30 minutes, the colour number of the EGC drops from 400 to 80, after 3 hours it is only 30.
All activated carbons adsorb from about 10 to 20% of the catalyst, depending on residence time.

EXAMPLE 2

In a further experiment carried out batchwise, 5 parts of EGC catalyst solution (99.7% EGC according to GC analysis, colour number 35, 1.21% by weight of $Et_4NBr$ as catalyst) and 1 part of activated carbon (Chemviron CPG LF, see Example 1) were contacted with one another at from 50° to 60° C. while stirring. After 30 minutes, a sample of the EGC was taken and freed of activated carbon residues. The Hazen colour number was then 10 and the catalyst content dropped by 5% compared with the starting sample.

EXAMPLE 3

The adsorption was carried out continuously on the activated carbon Chemviron CPG LF in a column (2 cm $\phi$) heated to 65° C., the EGC to be purified being passed through in the flooded state from the top downwards at constant volume flow. At intervals of a few hours in each case, instantaneous samples of the outflow were taken and analysed.

The EGC used had a colour number of 80 (bed height 16 cm, 50 ml bed volume, bulk density 0.46 g/ml$_{bed}$, drying of the activated carbon prior to commencement of the experiment for 36 hours at 130° C., nitrogen, 10 min. residence time).

7.1 l of the EGC having a colour number of 80 were purified in this experiment over 50 ml of Chemviron CPG LF to a colour number of at most 55 (142 times the volume of the adsorption bed). At the beginning of the experiment, 2 l of eluate having a colour number of only 35 to 40 was even obtained.

What is claimed is:

1. A process for the continuous or batchwise purification of ethylene glycol carbonate (EGC) containing impurities from the production or work-up process of the EGC, wherein the contaminated EGC is subjected at 40°–250° C. and at 1–200 bar to a treatment with activated carbon having a BET surface area of 200–3,000 m$^2$/g.

2. The process of claim 1, wherein the treatment is carried out at 40°–200° C.

3. The process of claim 2, wherein the treatment is carried out at 40°–160° C.

4. The process of claim 1, wherein the treatment is carried out at 1°–100 bar.

5. The process of claim 4, wherein the treatment is carried out at 1°–30 bar.

6. The process of claim 1, wherein the activated carbon has a BET surface area of 300°–2,000 m$^2$/g.

7. The process of claim 6, wherein the activated carbon has a BET surface area of 500°–1,500 m$^2$/g.

8. The process of claim 1, wherein the EGC to be purified is a bleed stream taken from the EGC reaction and work-up circuit to avoid accumulation of impurities or is a bleed stream from the residue of the EGC work-up or is both bleed streams.

9. The process of claim 8, wherein the bleed stream contains, besides impurities, the catalyst from the EGC production process and the treatment with activated carbon at the same time effects the partial removal of the catalyst.

10. The process of claim 9, wherein the bleed stream is fed only partially to activated carbon purification or wherein in this purification only partial removal of the secondary components is brought about or wherein both the only partial feed and the only partial removal are carried out.

11. The process of claim 8, wherein the bleed stream purified by treatment with activated carbon is recycled into the reaction and work-up circuit in the EGC production process.

12. Process of claim 1, wherein the activated carbon is arranged in a fixed bed.

13. The process of claim 1, wherein filtration is carried out after the adsorption step.

14. The process of claim 1, wherein the purification takes place with exclusion of moisture.

15. The process of claim 1, wherein the activated carbon used has a bulk density between 250 and 550 g/l.

16. The process of claim 1, wherein the activated carbon used has been prepared from sawdust and other wood wastes, straw, types of coal, nut shells, mineral oil tars, lignin, polysaccharides, polyacrylonitrile, bones, peat or coke products from brown or black coals.

17. The process of claim 16, wherein the activated carbon used has been prepared from wood, cellulose, lignin, bituminous or brown coal, peat or black coal coke.

* * * * *